United States Patent [19]
Porter et al.

[11] Patent Number: 5,912,178
[45] Date of Patent: Jun. 15, 1999

[54] PASSIVE MEASUREMENT OF ISOTOPES TO MONITOR HEALTH

[75] Inventors: Warren P. Porter; Isabel W. Treichel; Mark E. Cook, all of Madison, Wis.

[73] Assignee: Wisconsin Alumni Research Foundation, Madison, Wis.

[21] Appl. No.: 08/197,416

[22] Filed: Feb. 16, 1994

[51] Int. Cl.$^6$ .................................................. G01N 35/08
[52] U.S. Cl. ................................ 436/55; 436/56; 436/57
[58] Field of Search ................................ 436/57, 55, 56, 436/804

[56] References Cited

U.S. PATENT DOCUMENTS

| | | | |
|---|---|---|---|
| 3,649,201 | 3/1972 | Scalan | 436/173 |
| 4,068,122 | 1/1978 | Schmidt et al. | 250/281 |
| 4,298,347 | 11/1981 | Walsh | 436/173 |
| 4,427,884 | 1/1984 | Anbar et al. | 250/283 |
| 4,792,526 | 12/1988 | Ouellette et al. | 436/29 |
| 5,012,052 | 4/1991 | Hayes | 250/288 |
| 5,314,827 | 5/1994 | Schmidt et al. | 436/106 |

FOREIGN PATENT DOCUMENTS 0253927  1/1988  European Pat. Off. .

OTHER PUBLICATIONS

Murnick, et al., "Laser–Based Analysis of Carbon Isotope Ratios", 263 *Science* 945–947 (Feb. 18, 1994).

Dagani, "Laser method measures carbon isotope ratios", *Chem. & Engin. News* (Feb. 21, 1994).

Lacroix, et al., "Comparison of . . . Glucose Oxidation by Means of $^{13}C/^{12}C$ Breath Test", in *Stable Isotopes,* Schmidt, et al. editors, pp. 393–398 (1982).

Jarvis, et al., "The effect of food . . . during moderate exercise", 24 *Medicine and Science in Sports and Exercise* 320–326 (1992).

Murphy, et al., "Non–invasive assessment . . . lipolysis using $^{13}CO_2$ breath test", 65 *Archives of Disease in Childhood* 574–578 (1990).

Schoeller, et al., "Stable isotopes . . . Human Food Web", 18 *Ecology of Food and Nutrition* 159–170 (1986).

Gautier, et al., "Endogenous substrate oxidation . . . in breath $^{13}CO_2/^{12}CO_2$", 74 *J. Appl. Physiol.* 133–138 (1993).

O'Leary, "Carbon Isotope Fractionation in Plants", 20 *Phytochemistry* 553–567 (1981).

*Primary Examiner*—Nina Bhat
*Attorney, Agent, or Firm*—Quarles & Brady

[57] ABSTRACT

Methods and apparatus are disclosed for determining the presence of a catabolic state in an organism (or collection of organisms) by measuring changes in isotopic ratios in biological materials obtained from them. Preferably, $^{13}C/^{12}C$ ratios are monitored for isotopically unenriched animals, such as by testing changes in the ratio in blood or breath.

7 Claims, 1 Drawing Sheet

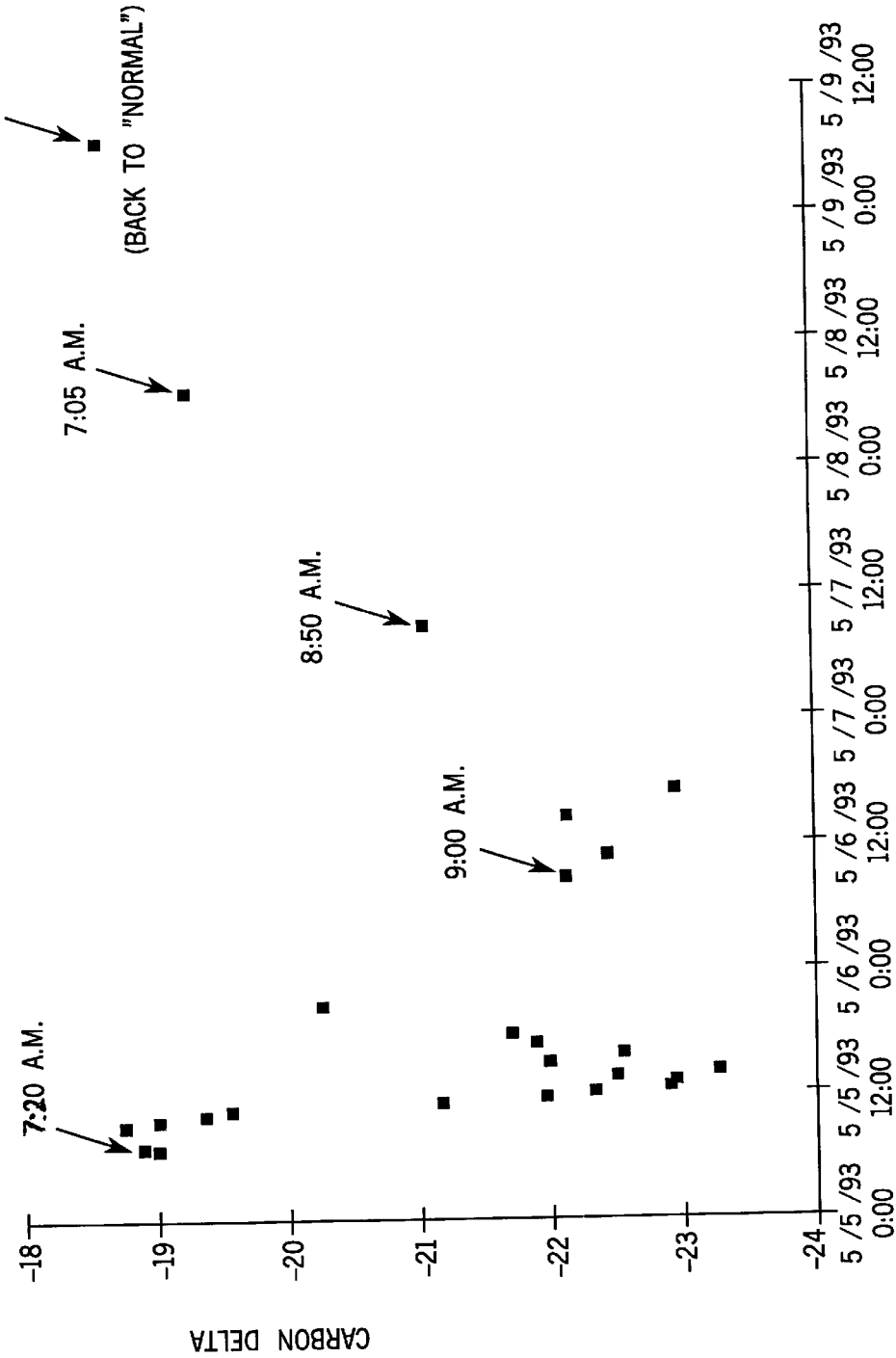

PASSIVE MEASUREMENT OF ISOTOPES TO MONITOR HEALTH

This invention was made with U.S. Government support awarded by the National Institutes of Health grant #GM 18938 and a DOE grant #DE-FG02-88ER 60633. The United States has certain rights in this invention.

FIELD OF THE INVENTION

This invention relates to methods and a system for measuring isotope ratios in order to analyze and monitor biological systems and/or organisms.

BACKGROUND OF THE INVENTION

Researchers have previously studied the isotopic ratio of $^{13}C/^{12}C$ in human breath. In these experiments, subjects were administered artificially labeled $^{13}C$ substrates before the study began. For example, Lacroix, et al., in *Stable Isotopes*, Schmidt, et al., editors, pp. 393–398 (1982) studied glucose metabolism during exercise as measured by $CO_2$ mass spectrometry after feeding $^{13}C$ labeled glucose to the subjects. The disclosure of this article and of all other publications referred to herein are incorporated by reference as if fully set forth herein.

Similarly in Klein, et al., European Patent Application No. 253,927 (January 1988) the inventors discussed feeding $^{13}C$ labeled urea to subjects in an attempt to detect the bacteria which cause ulcers. Urease activity in ulcer bacteria converts urea to carbon dioxide and ammonia. Breath samples were collected from the test subjects and analyzed for the presence of labelled isotope in exhaled carbon dioxide.

Jarvis, et al., 24 *Medicine and Science in Sports and Exercise* 320–326 (1992) discloses the effect of different food matrixes labeled with $^{13}C$ on breath $CO_2$ isotopic ratios during moderate exercise and Murphy, et al., 65 *Archives of Disease in Childhood* 574–578 (1990) discloses the use of isotopic ratios in breath $CO_2$ to test for lipase activity in the human gut after feeding the subjects fat labeled with $^{13}C$.

U.S. Pat. No. 4,298,347 discusses a method for analyzing isotopic ratios in exhaled carbon dioxide when performing the above type of studies. The method involves a solvent and an organometallic compound that reacts with gaseous carbon dioxide and forms a soluble carbonyl compound which has a unique and well separated infrared spectral peak for the $^{12}C$ and $^{13}C$ or $^{15}N:^{14}N$ products in the carbonyl frequency.

Schoeller, et al., 18 *Ecology of Food and Nutrition* 159–170 (1986) compares dietary isotopic ratios with the isotopic ratios in human plasma and hair. The article notes that the diet/tissue isotopic carbon ratio differences observed were small.

Gautier, et al., 74 *Journal of Applied Physiology* 133–138 (1993) studied the effect of the potent lypolysis inhibitor Acipimox by determining to what extent this affects the $^{13}C:^{12}C$ ratio in expired air $CO_2$ while the subject engaged in exercise. They concluded that if feeding experiments are done during exercise, a control should be run to correct for the effect of the exercise.

Researchers in the field often represent isotopic ratios as $\delta^{13}C0/00=(R_u/R_s-1)\times 1000$ where $R_u$ and $R_s$ are the $^{13}CO_2$ to $^{12}CO_2$ ratios of the sample and belemnite from the Pee Dee Formation in South Carolina respectively.

Notwithstanding this art, we believe that no one else to date has used monitoring of $^{13}C:^{12}C$ (or nitrogen stable isotope pairs) in isotopically unenriched subjects as a diagnostic tool.

SUMMARY OF THE INVENTION

The inventors have surprisingly discovered that the relative health of an essentially isotopically unenriched animal (or group of animals, or culture of microorganisms) can be determined by comparing the $^{13}C:^{12}C$ or $^{15}N:^{14}N$ relative amounts (e.g. via a ratio) in a sample from an animal or microorganism with a base line relative amount.

In one aspect, the invention provides a method of determining the presence of a catabolic state for an essentially isotopically unenriched animal. One collects at least a first sample from the animal and measures the relative amount of a first isotope to a second isotope in the sample. The first and second isotopes are the pair $^{13}C$ and $^{12}C$, or are the pair $^{15}N$ and $^{14}N$. One then compares the relative amount with a corresponding base line relative amount of said pair of isotopes in a specimen other than the sample. At least one of the specimen and sample is not derived from the breath of an animal.

The base line relative amount can be the relative amount of the isotopes in an earlier specimen of the same type from the animal (e.g. a current whole blood test v. an old whole blood test), or can be from a contemporaneous test of another type of specimen in the animal (e.g. breath v. hair).

Preferably, the one sample from the animal is selected from a group consisting of breath, whole blood, blood immunoglobulin, hemoglobin, urine, hair, tissue, feathers, horns, hooves, nails, skin, shells, and membranes. Also preferably, the relative amount from the sample is determined using a mass spectrometer and the pair of isotopes are $^{13}C$ and $^{12}C$.

In another aspect, the invention provides a method of determining the presence of a catabolic state in an essentially isotopically unenriched population of at least a plurality of animals or microorganisms in an enclosure. One collects at least one sample of air from the enclosure and measures the relative amount of a first isotope to a second isotope in the sample. The isotopes are the pair $^{13}C$ and $^{12}C$, or are the pair $^{15}N$ and $^{14}N$. One then compares the relative amount with a corresponding base line relative amount of said pair of isotopes. Preferably, the enclosure is an animal housing facility, and the relative amounts for at least the sample are measured using a mass spectrometer.

In yet another aspect, the invention provides an apparatus for analyzing a gaseous sample. There is a machine (e.g. a mass spectrometer) for measuring the relative amounts of $^{13}C$ and $^{12}C$ in the sample; a link from the machine for transmitting the relative amount data; and a computer for receiving the relative amount data and comparing it with a data base containing relative amount base line data for a source of the sample. There is also a display for displaying a comparison of the base line and the sample's relative amount. A preferred mass spectrometer is the Finnigan MAT-IRMS. A preferred computer is the PC compatible 386 or greater. A preferred link is an output from the mass spectrometer to the computer. A preferred data base system is the Isodat software system. A preferred display is the screen for the computer.

Preferably, there is also means for generating a warning signal when the comparison deviates from selected parameters. To achieve this, a PC could be coupled to the output from a mass spectrometer, with the PC having in memory data for an accepted range for the particular patient/ enclosure. A warning or electrical signal (e.g. bell, printout) could be triggered when defined parameters from the base line are exceeded for that source. Changes could trigger further inspection or further sampling, or even electrical signals operating other machines and instruments. Typically a 0.5 or greater change in $\delta^{13}C0/00$ for a human patient merits attention.

The term "essentially isotopically unenriched", as used herein, means that the animals (or cultures) are not being artificially provided by those working with the tester with $^{13}C$ if $^{13}C/^{12}C$ is being tested, or $^{15}N$ if $^{15}N/^{14}N$ is being tested. Thus, if $^{13}C/^{12}C$ is being evaluated, $^{15}N$ additions would not constitute "enrichment" for this purpose. Further, background $^{13}C$ or $^{15}N$ obtained in amounts naturally present in foods would not be considered enrichment.

The baseline isotopic relative amount for the animal or population would preferably be that of an optimal (or at least satisfactory) condition. In the alternative, it can simply be a reading at a first selected time. Preferably the isotopic ratios are determined from a gas sample by a chromatograph-mass spectrometer apparatus. The gas can be directly produced by the animal, or liquid or solid samples can be converted to gas.

Note that by testing two different types of samples from the same animal at essentially the same time (e.g. hair versus breath), information about the timing of the change of health can be obtained.

The objects of the invention therefore include:

(a) using measurements of the relative amounts of certain stable isotopes to determine if an animal is abnormally catabolizing self (cachexia) as a result of infection, stress, cancer, nutrient deficiency, altered organ function, or other undesired causes;

(b) using measurements of the relative amounts of certain stable isotopes to determine how long an animal or other organism has been catabolic or anabolic;

(c) using measurements of the relative amounts of certain stable isotopes in the atmosphere of an animal or microorganism enclosure to monitor overall health of the population in the enclosure, so as to thereby create a biosensor to control feeding, ventilation, or alarm equipment; and (d) using measurements of the relative amounts of certain stable isotopes as a sensitive indicator of stress related health status problems.

A particular object of the present invention is to conduct such monitoring without the need for artificially providing the animals or cultures with the isotopes to be measured. These and still other objects and advantages of the present invention will be apparent from the description below.

BRIEF DESCRIPTION OF THE DRAWING

The FIGURE is a graph plotting $\delta^{13}C0/00$ in breadth samples versus time for a mouse injected with an endotoxin.

DESCRIPTION OF THE PREFERRED EMBODIMENTS

The present invention focuses on sampling an animal, or a population of animals (e.g. chickens in a chicken coop), or a microorganism culture (e.g. yeast; virus; bacteria), to determine relative amounts of certain stable isotopes (e.g. $^{13}C/^{12}C$). One uses a change in the relative amount as a predictor of health and well being. One comparison uses two samples of the same type of material (blood at the present time v. blood at an earlier time). The present invention is especially well suited for intensive care unit monitoring, such as where breath sampling may supplement continuous cardiac monitoring.

A comparison can also be made of two or more different types of materials at substantially the same time (breath v. blood IgG v. hair). This provides a forensic guide as to the timing of the adverse change.

We have learned that conditions such as infection, cancer, diet deficiency, toxic chemical exposure, stress, or impaired function of organ systems cause these ratios to shift from healthy status levels. The baseline isotope ratio usually corresponds to a specific individual person or population, but for standard repeated microorganism culturing the base line may be selected based on experience ratios for prior cultures.

Importantly, the methods employed by the invention do not require isotope enrichment. They are based on the natural presence of the isotopes in diet and organism tissues. The method allows for a rapid, non-invasive determination of net catabolic processes (i.e. cachexia) of animals and humans experiencing altered organ function, or a state in which nutrient intake is at a deficit. Any condition in which the organism is catabolizing self instead of diet can be detected by the described methods.

Changes in the $^{13}C/^{12}C$ and/or $^{15}N/^{14}N$ ratios indicate a stress on the animal. In some cases, the ratio increases. In other cases, the ratio decreases. However, either type of change is of concern.

Gas (e.g. breath) samples can be readily tested on a mass spectrometer (e.g. $CO_2$, $N_2$). For solid or liquid samples that contain carbon, carbon can be converted to $CO_2$. This is usually done by burning the liquid or solid, but bicarbonate blood assays also can generate $CO_2$ directly from blood. For solid or liquid samples containing N, it is preferred to convert the samples to gas using a technique such as digesting the sample with concentrated $H_2SO_4$ (Kehldahl) to form $NH_3$, then steam distilling the $NH_3$ into dilute sulfuric acid, and then oxidizing the $(NH_4)_2SO_4$ solution with NaOBr to form $N_2$.

The invention provides a means for earlier diagnosis of a problem/disease, more effective monitoring of intensive care patients, analyzing the effect of environmental stress on humans and animals, another means of testing toxicity, and even a means of evaluating the health status of wild species.

When an animal is under normal, non-stressful conditions, its metabolism uses newly consumed food (without significant resort to stored resources). The normal substrates from metabolism are carbohydrates that are absorbed from the gut. Under stress, an animal's metabolism is catabolic and they begin using their own reserves which are principally proteins and lipids.

Stored protein tends to contain more of the heavier isotopes (e.g. $^{13}C/^{12}C$ is higher) than carbohydrates. Fats have less heavy isotopes than both proteins and carbohydrates. Thus, differences in what is being metabolized show up quickly as differences in the ratios.

Note that the ratios will be different in disease status for proteins which rapidly turn over (i.e. blood immunoglobulin), versus those which turn over slower (i.e. hemoglobin), versus those that turn over even slower (keratin of hair, horns, hooves or the baleen of whales). This permits one to forensically test a patient in a single office visit to determine to some extent when a problem started (without the need for a healthy status base line). This uniquely helps a doctor correlate a disease state to the timing of events in a patient's life.

During a catabolic state (such as one due to infection, cancer, diet deficiency, toxic chemical exposure, impaired function of organ systems for normal body function, or high stress), the organism must use body stores of carbohydrates, amino acids, or fats as a source of energy for maintenance, thereby generating urinary nitrogen and $CO_2$ in breath. Thus, changes will show up quickly in urine and breath. Body carbohydrates, amino acids, and fats are also a source of nutrients to synthesize products, e.g. immunoglobulins, that are a function of the catabolic state.

During photosynthesis, plants use $CO_2$ from the air and produce carbohydrates, fat, and proteins which are usually depleted in $^{13}C$. This discrimination against $^{13}C$ results in foods that are significantly depleted in $^{13}C$ relative to $^{12}C$. That general picture is further refined because of the relative amount of synthesis required for carbohydrates, fats, and proteins. In any one plant, the carbohydrates are more depleted of $^{13}C$ than proteins, because of greater synthetic activity needed to produce them (more opportunities to discriminate between isotopes). Fats require the greatest amount of synthetic steps and are accordingly the most depleted in $^{13}C$ of all three basic organic molecules.

It is important to note that when food absorbed from the gut is used as a fuel source, the surplus not needed for fuel is incorporated as a slightly heavier (more $^{13}C$ and $^{15}N$) protein molecule, because the lighter isotopes tend to be incorporated into breath $CO_2$ or be otherwise disposed of. A diet will tend to be (from heaviest to lightest) protein (heaviest due to little synthesis since amino acids are apparently incorporated directly from diet protein to organism protein), carbohydrates (next lightest because of some synthetic activity in their construction), and fats (lightest because they undergo the most synthetic steps before being incorporated in body tissues).

When the animal or human has a dietary intake of nutrients that meet or exceed the need for maintenance and production (i.e. growth and reproduction), then stored carbohydrates in food are primarily used as the daily fuel source. In this normal or preferred situation, the carbon, nitrogen, and oxygen in breath $CO_2$, carbon and nitrogen in urine, and the carbon in rapidly turning over proteins (i.e. immunoglobulin), resembles the isotope level in the normal diet.

By contrast, in the situations when the organism is dependent on its own stored tissue components (amino acids, proteins, and carbohydrates) as a fuel source, then the carbon, nitrogen, and oxygen in breath $CO_2$, carbon and nitrogen in urine, and carbon in rapidly turning over proteins (i.e. immunoglobulin) resemble the isotopic abundance found in the amino acids, fats, and carbohydrates of the organism itself.

A slight complication is due to the possible presence of minor amounts of higher weight isotopes of O when testing $CO_2$ (e.g. $^{17}O$). However, the natural presence of $^{17}O$ is low.

EXAMPLE 1

A deer mouse was injected with 1 mg/kg body weight of endotoxin. The $\delta^{13}C0/00$ value (Delta) from expired $CO_2$ was determined over time. See FIG. 1. The anabolic (recovery) state began at approximately 32 hours post endotoxin injection.

The exhaled air could have been tested using the U.S. Pat. No. 4,248,347 system, but for greater sensitivity, repetitiveness of response, and ease and speed of detection we chose to do real time isotope ratio mass spectrometry by directly collecting the gas without chemically preprocessing the sample, and then test the sample in an isotope ratio mass spectrometer.

EXAMPLE 2

Cows that are lactating heavily, especially early after birth, use body tissue to help in milk production and are thus naturally catabolic. Dry cows are anabolic. We used three measures of the metabolic state of the animals: a short term (3 day turnover) protein-IgG, a longer lifetime (3 months) protein-hemoglobin, and hair samples from the tails of both cows. Hair growth at the tail tip is about 3 inches per year. The hair fibers from each cow were cut to determine recent nutritional state (part of the hair fiber near the skin) and past nutritional state (part of the hair fiber near the tip). All protein samples were ashed in sealed glass tubes in a furnace to obtain the $CO_2$ for analysis. The collected $CO_2$ was cryogenically purified and fed into a Finnigan MAT Delta E Isotope Ratio Mass Spectrometer to obtain $^{13}C/^{12}C$ rations.

EXAMPLE 3

To test blood, one can add $H_3PO_4$ to the blood, and collect $CO_2$ as it bubbles off and then treat the gas as before.

EXAMPLE 4

To test $^{15}N/^{14}N$ in urine one digests the proteins with concentrated sulfuric acid and steam distill the $NH_3$ formed into dilute sulfuric acid. The resulting $(NH_4)_2SO_4$ solution is then oxidized with NaOBr to form $N_2$. The $N_2$ gas is used to measure the $^{15}N/^{14}N$ ratio.

OTHER EXAMPLES

We have also tried our technique on bird egg shells and egg membranes, materials from lizards, and bacteria culture from cow rummen.

Industrial Applicability

Commercial applications include, without limitation, intensive care unit breath monitoring systems, diagnostic tests for a doctor's office (multiple blood or urine tests), and a monitoring/warning system for an enclosure housing chickens or a microorganism culture.

Although the present invention has been described with reference to certain preferred embodiments, other versions are possible. For example, other biological fluids, tissues or materials (gas, liquid, solid) may be analyzed. Carnivores or omnivores are the preferred animals, but herbivores can be tested as well. Therefore, the scope of the claims is not to be limited to the description of the preferred versions contained herein.

We claim:

1. A method of determining the presence of a catabolic state in an essentially isotopically enriched animal, comprising the steps of:

collecting a sample selected from the group consisting of breath, whole blood, blood immunoglobin, hemoglobin, urine, hair tissue, feathers, horns, hooves, nails, skin, shells and membranes from the animal;

measuring the relative amount of a first isotope to a second isotope in the sample;

the isotopes being the pair $^{13}C$ and $^{12}C$, or being the pair $^{15}N$ and $^{14}N$;

comparing said measured relative amount of the sample with a relative amount of said pair isotopes in a comparison specimen other than the sample; and determining from the comparison step whether a catabolic state is present in the animal wherein the change in the isotope ratios either increasing or decreasing is indicative of a catabolic state.

2. The method of claim 1, wherein at least one relative amount is determined using a mass spectrometer.

3. The method of claim 1, wherein the pair of isotopes are $^{13}C$ and $^{12}C$.

4. A method of determining the presence of a metabolic state in an essentially isotopically unenriched population of at least a plurality of animals or microorganisms in an enclosure, comprising the steps of:

collecting a sample of air from the enclosure;

measuring the relative amount of a first isotope to a second isotope in the sample;

the isotopes being the pair $^{13}C$ and $^{12}C$, or being the pair $^{15}N$ and $^{14}N$;

comparing the measured relative amount with a warning level relative amount of said pair of isotopes; and determining from the comparison whether a catabolic state is present in the population.

5. The method of claim 4, wherein the pair is $^{13}C$ and $^{12}C$.

6. The method of claim 5, wherein the enclosure is an animal housing facility.

7. The method of claim 6, wherein the relative amount for the sample is measured using a mass spectrometer.

* * * * *

UNITED STATES PATENT AND TRADEMARK OFFICE
CERTIFICATE OF CORRECTION

PATENT NO. : 5,912,178

DATED : June 15, 1999

INVENTOR(S) : Warren P. Porter
Isabel W. Treichel
Mark E. Cook

It is certified that error appears in the above-identified patent and that said Letters Patent is hereby corrected as shown below:

At claim 1, line 2, replace [enriched] with unenriched.

At claim 1, line 6, replace [hair] with hair,.

At claim 1, line 13, replace [pair isotopes] with pair of isotopes.

At the end of claim 1, replace [.] with ; wherein at least one of said specimen and said sample is not derived from the breath of an animal.

At claim 4, line 1, replace [metabolic] with catabolic.

Signed and Sealed this

Thirtieth Day of November, 1999

Q. TODD DICKINSON

Attest:

Attesting Officer

Acting Commissioner of Patents and Trademarks